United States Patent [19]

Göhrich et al.

[11] 4,158,143
[45] Jun. 12, 1979

[54] TUBE FOR IRRADIATION EQUIPMENT

[75] Inventors: Klaus Göhrich, Küssaberg, Fed. Rep. of Germany; Heinz Vogt, Oberehrendingen, Switzerland

[73] Assignee: BBC Brown, Boveri & Company Limited, Baden, Switzerland

[21] Appl. No.: 894,509

[22] Filed: Apr. 7, 1978

[51] Int. Cl.² .......................... G02B 5/00; G21K 1/00; H01J 1/52; H01J 3/00
[52] U.S. Cl. ..................................... 250/505; 250/511
[58] Field of Search ............... 250/505, 511, 512, 513

[56] References Cited

U.S. PATENT DOCUMENTS

| | | | |
|---|---|---|---|
| 3,942,019 | 3/1976 | Claridge et al. | 250/512 |
| 4,034,228 | 7/1977 | Araunor | 250/511 |
| 4,053,808 | 10/1977 | Peacock | 250/505 |

*Primary Examiner*—Craig E. Church
*Assistant Examiner*—Thomas P. O'Hare

*Attorney, Agent, or Firm*—Oblon, Fisher, Spivak, McClelland & Maier

[57] ABSTRACT

A tube for irradiation equipment for limiting an emergent beam, with a baseplate, possessing a central aperture, intended for attaching to the equipment, as well as four carrier plates, each of which possesses a limiting edge and a sliding edge located at right angles thereto. The carrier plates are located parallel to the baseplate, the limiting edge of each carrier plate resting against the sliding edge of the adjacent carrier plate and each of the two mutually opposite pairs of carrier plates being displaceable, parallel to the direction of its sliding edges and symmetrically to the center of the transmission aperture, for the purpose of continuously varying the transmission aperture defined by the limiting edges, during which displacement each of the displaced carrier plates carries with it the carrier plate, resting against the limiting edge of the former plate, parallel to the direction of the limiting edge of the latter plate.

8 Claims, 5 Drawing Figures

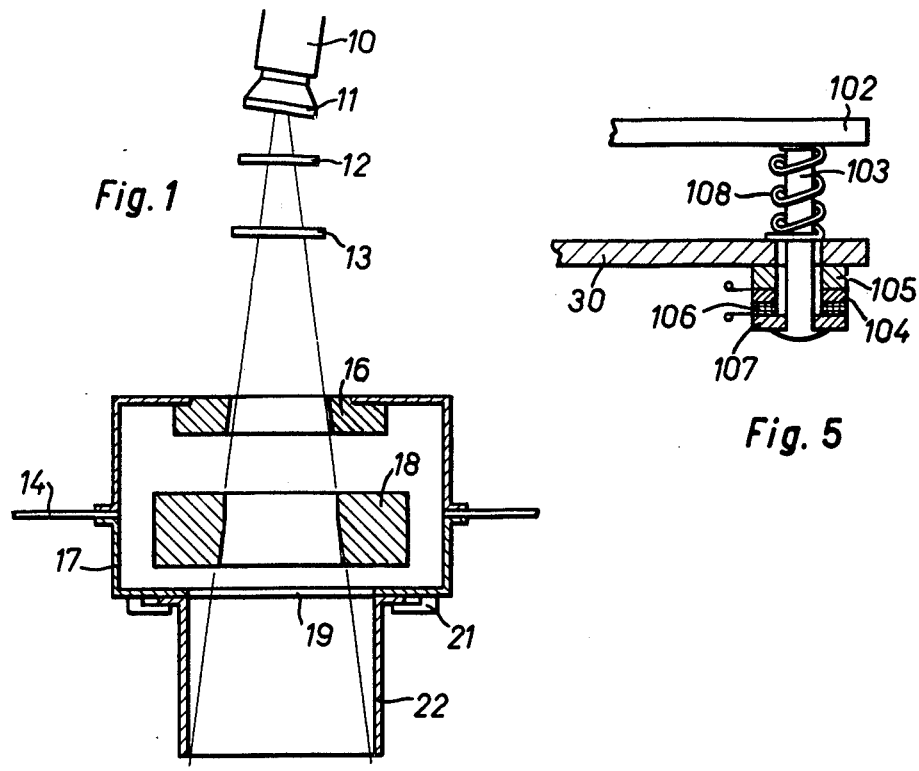
Fig. 1
Fig. 5
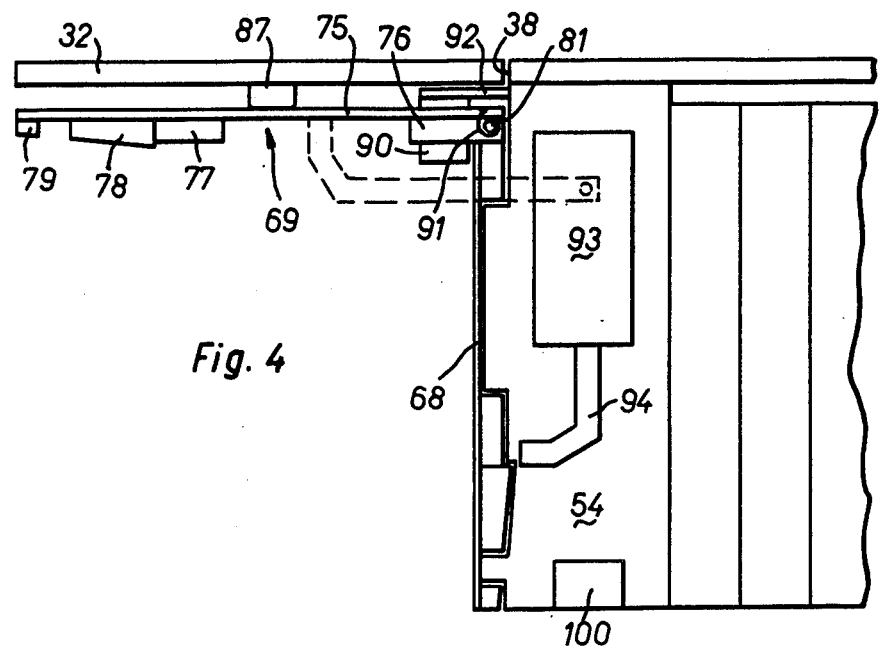
Fig. 4

TUBE FOR IRRADIATION EQUIPMENT

BACKGROUND OF THE INVENTION

The present invention relates to a tube for irradiation equipment for limiting an emergent beam.

The term irradiation equipment is in particular applied, in the text which follows, to particle accelerators, electron accelerators, gamma irradiation equipment and X-ray equipment. For therapeutic and diagnostic use it is essential to limit the cross-section of the beam emerging from the irradiation equipment to the requisite minimum and to screen off the irradiation effectively, at the sides, between the outlet aperture of the irradiation equipment and the surface of the article to be irradiated. At the same time, when using an electron accelerator the proportion of the secondary X-rays and scattered electrons produced by the high speed electrons in the diaphragm system, and manifesting itself outside the actual field of irradiation, should be kept as low as possible in order to reduce the side-effect of the irradiation.

As a further condition, it should be possible to choose as many variations of field dimensions as possible within the range of field sizes imposed by the irradiation equipment. For this reason a variety of devices have also already been disclosed and are used with which the cross-section of the irradiation can be limited and the beam can be screened off laterally.

A first known device consists of a set of diaphragms, of which each is firmly fixed to a tube. The diaphragm and tube can be fixed detachably to the casing of the electron accelerator. For example, the diaphragms are in the form of thick lead sheets which have a central aperture which limits the cross-section of the emergent electron beam. The tube serves to limit the electron beam and screen it off laterally. This relatively simple device suffers from several disadvantages. It is only possible to adjust the beam to fixedly predetermined cross-sections, and the exchangeable diaphragms with attached tube require a great deal of storage space, are expensive, are difficult to handle because of their weight, and must, whenever a change in beam cross-section is necessary, be exchanged, thereby consuming a relatively large amount of time.

Another known device comprises a baseplate on which several diaphragms are located in succession in the direction of the beam. Each of these diaphragms has several diaphragm blocks continuously displaceable at right angles to the direction of the beam. This device permits continuous variation of the diaphragm cross-section and hence of the effective electron beam and does not require an additional tube. A disadvantage of this device is that because of the diaphragms being arranged in succession, a part of the fast electrons is screened off near the object to be irradiated, as a result of which a relatively high proportion of gamma radiation and secondary electrons is liberated, which must be avoided particularly in the case of radiation therapy, and that if the diaphragm aperture is small the diaphragm blocks project beyond the cross-section of the useful electron beam, which makes it difficult, or even impossible, to introduce the device into recesses and, for example, to irradiate the armpits or the throat.

Further, a device is already known which possesses a variable diaphragm built into the accelerator casing, and corresponding tubes of different cross-section which can be attached to the accelerator housing. In this device, the advantages of the variable diaphragm can only be utilized partially because the diaphragm must necessarily be set to the dimensions of the available tubes. Furthermore, this device suffers from all disadvantages already mentioned above for exchangeable tubes.

SUMMARY OF THE INVENTION

Accordingly, it is the object of the present invention to provide a tube for irradiation equipment, which tube is of infinitely variable cross-section, and in which the external dimensions of the free end are only slightly greater than the dimensions of the free aperture at the end of the tube, in order to permit, as far as possible, unhindered approach to the object to be irradiated.

According to the invention, this object is achieved by means of a tube of the initially described type, which is characterized in that on each carrier plate there are provided a side wall and at least one equally high lamella, which side wall projects, at the side of the limiting edge which abuts the sliding edge, at right angles from the carrier plate and which lamella or lamellae is or are pivotably fastened in the region of the limiting edge and can be laid down on the carrier plate or be erected, as an extension of the side wall, in order to form a side wall of a tube of variable cross-section.

The new tube can be fed to any quadrangular cross-section with dimensions between a minimum square, the side length of which corresponds to the length of one side wall, and a maximum square, the side length of which corresponds to the length of one side wall and of the corresponding lamellae. Because the lamellae not required to form the tube side walls are laid down on the carrier plates, the external cross-section of the tube is only slightly greater than the internal cross-section, thereby permitting unhindered introduction of the tube into recesses.

For simpler manual adaptation of the tube walls to the selected cross-section, a plurality of magnets can be fixed to each carrier plate, which magnets hold the lamellae laid down on the carrier plate, while a spring can engage against the base of each lamella, which spring pivots the lamellae, released by the holding magnets, into the erect position.

In a preferred embodiment, further measures are provided which, on adjusting the tube cross-section, automatically raise the lamellae or lay them down on the carrier plate. For this purpose there is fixed to each carrier plate along the extension of the limiting edge, a tongue, which carries on its end projecting onto the adjacent carrier plate a stop of which one side face rests against the adjacent erect lamella and prevents its pivoting into the laid-down position, while its other side face has a wedge-shaped chamfer and is pushed under the adjacent laid-down lamella and, on displacing the carrier plate in order to increase the transmission aperture, lifts this next lamella off the holding magnet. Furthermore, an electromagnetic switch device is fixed on each side wall, which possesses a lever which, after the carrier plate has been displaced in order to reduce the transmission aperture, pivots the lamella adjoining the side wall, on the adjoining carrier plate, into the laid-down position.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 shows the schematic representation of an accelerator window with diaphragms and a tube of the hitherto conventional type, FIG. 4 shows the side view, partially in section, of the tube according to FIG. 2, viewed in the direction of the arrow IV, and FIG. 5 shows the schematic representation of a contact switch in the tube baseplate.

DESCRIPTION OF THE PREFERRED EMBODIMENTS

Figure 2:
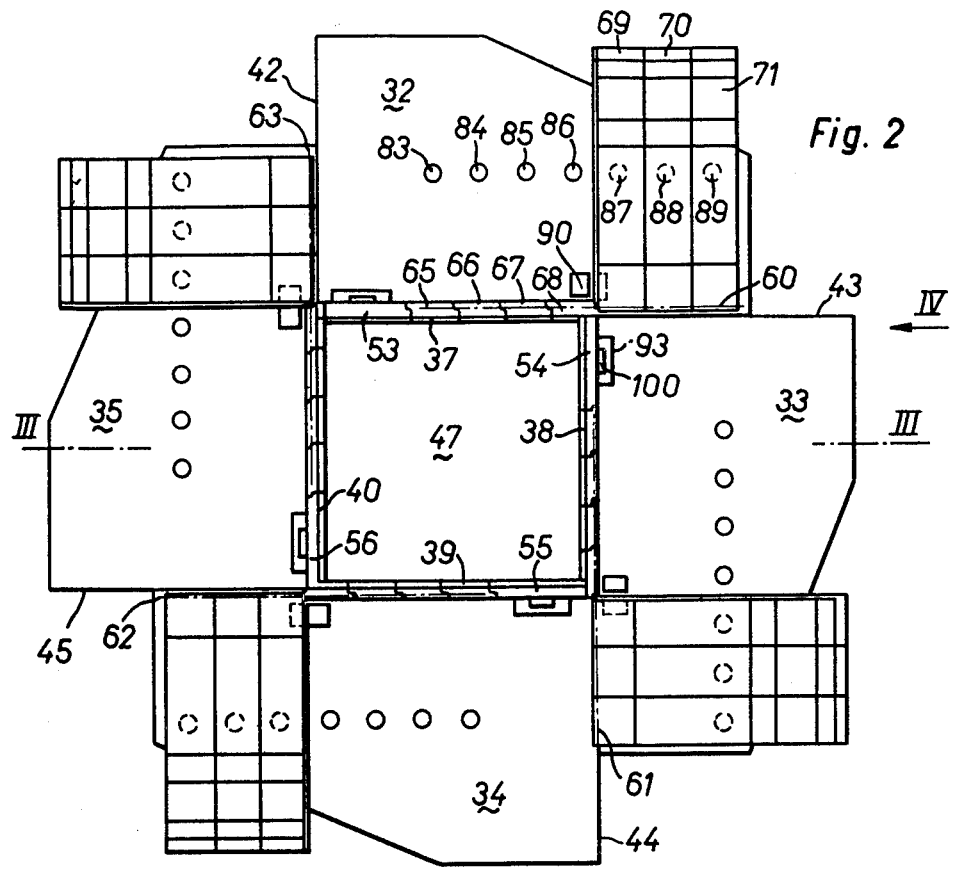
FIG. 2 shows the plan view of an embodiment of the new tube.

Referring now to the drawings, wherein like reference numerals designate identical or corresponding parts throughout the several views, FIG. 1 shows schematically the aperture of an electron accelerator with diaphragms for the electron beam, and a tube. Accelerator 10 possesses a window 11 which is intended to transmit a narrow electron beam. At a distance from the window, in the direction of the emergent electron beam, are located a first scatterer 12 and a main scatterer 13, which broaden the narrow electron beam. In order to limit the maximum diameter of the electron beam issuing from the accelerator casing 14, a first diaphragm 16 is fixed within the casing. Furthermore, a screen 17 is provided, which screens off an anterior diaphragm 18, located in the region of the aperture of the casing, and possesses a central aperture 19 through which the electron beam emerges from the accelerator casing. This central aperture is framed by a holder device 21, into which an exchangeable tube 22 is inserted.

In order to adapt the cross-section of the electron beam emerging from the tube to the intended use, it is possible to use, in this arrangement, anterior diaphragms 18 of different free internal cross-sections or a fixedly built-in anterior diaphragm with a variable free internal cross-section, as well as to use exchangeable tubes matching these cross-sections.

Figure 3:
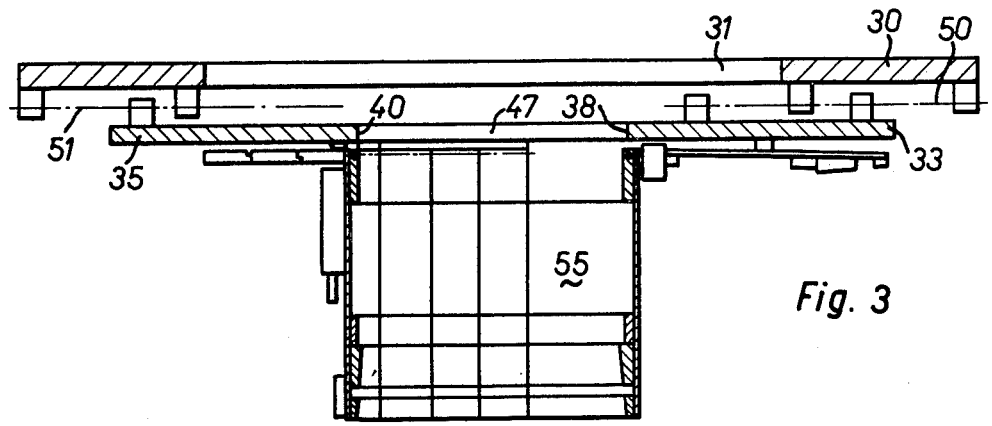
FIG. 3 shows the section along line III—III through the tube according to FIG. 2.

The embodiment of the tube of variable cross-section, according to the invention, shown in FIGS. 2 and 3 is built up on a baseplate 30. The baseplate is intended for fixing to the screen 17 and has a large central aperture 31. Four carrier plates 32, 33, 34 and 35 are located on the baseplate. Each carrier plate has at least two edges located at right angles to one another, namely a limiting edge 37, 38, 39 or 40 and a sliding edge 42, 43, 44 or 45. The carrier plates are so located relative to one another that the parts of the limiting edges which adjoin the sliding edges form the framing of a transmission aperture 47 and the remaining part of each limiting edge rests against the sliding edge of an adjacent carrier plate. The carrier plates can be displaced parallel to the plane of the baseplate by means of a displacement device customary for adjustable anterior diaphragms, which device is known to those skilled in the art and is therefore only indicated with broken lines 50, 51. This displacement device permits each of the two pairs of carrier plates, formed by mutually opposite carrier plates 32, 34 or 33, 35, to be displaced symmetrically to the center of the transmission aperture 47, independently of the other pair of carrier plates, and in the direction of its sliding edge. During this displacement, the two carrier plates of the other pair of carrier plates are carried with the first pair, so that the contact between adjacent carrier plates and the framing of the transmission aperture always remains preserved. If, for example, the carrier plates 33, 35 are pushed apart, the carrier plate 34 follows the displacement of the carrier plate 33 and the carrier plate 32 follows the carrier plate 35. In this way, the square transmission aperture 47 shown in FIG. 2 can be reduced and enlarged or be reshaped into an upright or horizontal rectangle of any desired dimensions.

As can be seen most clearly in FIG. 2, a side wall 53, 54, 55 or 56 projects from each carrier plate. Each side wall is located along the limiting edge and one of its lateral edges terminates in the corresponding sliding edge of the carrier plate. Each side wall stands at right angles to the carrier plate and the four side walls form a closed tube if the four carrier plates are pushed together sufficiently far that in their limiting edges frame the smallest envisaged transmission aperture. In the lateral extension of each side wall, and above the limiting edge, there is additionally fixed a thin shaft 60, 61, 62 or 63. On this shaft a plurality of lamellae are pivotably mounted, of which, for clarity, only lamellae 69 to 71 on the shaft 60 of the carrier plate 32 are identified by reference numbers. All lamellae can be pivoted between a laid-down position in which they are located virtually parallel to the surface of the carrier plate, and an erect position, in which they are located parallel to the side wall. In FIGS. 2 and 3, the lamellae 65 to 68 on the carrier plate 32 (and the corresponding lamellae of the other carrier plates) are drawn in the erect position, and the lamellae 69, 70 and 71 on the carrier plate 32 (as well as the corresponding lamellae of the other carrier plates) are drawn in the laid-down position. As will be immediately obvious to anyone skilled in the art, it is possible, by erecting those lamellae which are located along the parts of the limiting edges which form the framing of the transmission aperture, to form a tube the internal cross-section of which is virtually of the same size and the same shape as the cross-section of the transmission aperture. Because the lamellae not required for broadening the tube walls remain in their laid-down position, the external cross-section of the free end of the tube is not much larger than its internal cross-section, that is to say, the cross-section of the electron beam which emerges through the tube. This construction makes it possible to introduce the free end of the tube, without hindrance by projecting side pieces, even into recesses. As has already been described above, this is particularly important when using irradiation equipment in medicinal diagnostics and therapy, for example if the tube is to be brought into an armpit or against the neck of a patient.

If the transmission aperture is set to a dimension which does not correspond to the grid predetermined by the lateral length of the lamellae, the last erect lamella of each side wall projects partially beyond the corner of the tube. This apparent disadvantage is virtually of no importance if the lateral length of the lamellae is not great.

As can be seen best in FIG. 4, each lamella consists of a steel strip 75, at one lengthwise end of which is located a lamella base 76, while in the region of its other lengthwise end there are located several absorption pieces 77, 78 and 79. The lamella base preferably consists of bearing metal and has a bore 81, by means of which the lamella is pushed onto the shaft 60. The absorption pieces are in particular intended to absorb secondary X-rays and stray electrons. In a combination which is particularly suitable for this purpose, the absorption pieces 77, 78 and 79 consist of light metal, steel or Antikorrodal.

In the embodiment of the new tube shown in the figures, a plurality of small permanent magnets is located on each carrier plate, among which, for clarity, only magnets 83 to 89 on carrier plate 32 are identified by reference numbers. These permanent magnets are provided in order to hold the lamellae which have been laid down on the carrier plate.

As may be seen from FIG. 2, the lamellae overlap in cross-section. The result of this is that the tube wall composed of adjacently located lamellae is "tight" and that none of the erect lamellae can be laid down as long as the last erect lamella is locked in its position. For this purpose, a thin tongue 92 is fixed to each carrier plate (FIG. 4) which tongue projects, in the extension of the limiting edge 38, beyond the adjacent carrier plate 32, and carries a stop 90. This stop rests, with one of its sides, against the particular last lamella 68 of a tube wall, and thereby prevents this lamella from being pivoted from the erect position into the laid-down position. Preferably, this stop is wedge-shaped in the direction of the sliding edge. This makes it possible, when displacing a pair of carrier plates in order to enlarge the cross-section of the framed transmission aperture 47, to slide the stops, fixed to the two displaced carrier plates, with their wedge-shaped surfaces under the lamellae 69 of the adjacent carrier plates 32 and to lift these lamellae off the permanent magnets 87.

To each lamella there is allotted a spring 91 which engages in the region of the base of the lamella (FIG. 4) and pivots it into the erect position as soon as it has been released from the holding magnet.

In the shown embodiment of the tube there is furthermore located, on the outside of each side wall 54, an electromagnetic switch device 93 which comprises a lever 94 which has a virtually vertical rest position and can be pivoted through about 90° into the working position shown with broken lines in FIG. 4. After displacing one pair of carrier plates in order to reduce the cross-section of the transmission aperture, the switch devices on the side walls of the displaced carrier plates are actuated, whereupon in each case the last lamella of the adjacent tube wall is pivoted into its laid-down position and is held by the corresponding permanent magnet. Because of the mutual overlap of the lamellae, which has already been mentioned above, laying down one lamella results in all further lamellae automatically being laid down in the direction facing away from the corresponding side wall. This ensures that on reducing the cross-section of the transmission aperture all lamellae no longer required to form the tube have been laid down on the corresponding carrier plate.

As has already been described above, it is necessary, when using irradiation equipment for diagnostics and therapy, to bring the free end of the tube as close as possible to the object or to the patient. Because of the large weight of the entire installation, special drive motors are used for the required displacement motions or rotary motions of individual parts of the equipment. In order to ensure that these drive motors are switched off as soon as the tube has been brought to a minimum distance from the patient, special proximity switches are used. In a first embodiment of such a safety device, an insulated electrode 100 is fixed to the free end of each side wall. The electrodes, numbering four in total, are preferably wired electrically in parallel, and form a capacitor with the tube. This capacitor is connected, in a known manner, to an HF measuring bridge which is put out of balance as the tube approaches a patient and switches off the feed voltage for the drive motors, via a comparator/trigger circuit, when a presettable unbalance has been reached.

In another embodiment of this safety device, the baseplate of the tube is fixed in an insulated manner to the accelerator casing, and the entire tube is used as a capacitor electrode.

In yet another embodiment, the safety device is actuated not on approaching, but only on touching, the object to be irradiated. As is shown schematically in FIG. 5, this embodiment uses a tube insert 102 which is located parallel to the baseplate 30 and can be inserted into the holding device 21. A stud bolt 103, which passes through a corresponding bore in the baseplate 30, is fixed to each of the four corners of this tube insert. In addition, an electrical switch is provided, of which one contact 104 is fixed by means of an insulating disc 105 to the baseplate, while its other contact 106 is fixed by means of an insulating disc 107 to the free end of the stud bolt. Around each stud bolt is inserted, between the tube insert 102 and the baseplate 30, a spring 108 which presses the baseplate away from the tube insert and presses the contact 104 onto the contact 106. The four switches are preferably wired electrically in series. When, on moving or turning the installation or the patient, the tube is touched and compressed or tipped against the force of one or more springs, the contacts of the corresponding switches are separated from one another and a safety circuit is broken and switches off the feed voltage for the drive motors.

In an embodiment of the new tube used in practice the side length of each side wall is 4 cm, which makes it possible to telescope the carrier plate sufficiently that the minimum transmission aperture 47 corresponds to a square with sides 4 cm long. Furthermore, with this embodiment 16 lamellae are located on each carrier plate, the side length of each lamella being 1 cm. Accordingly, the maximum transmission aperture can be set to correspond to a square with sides 20 cm long. As has already been described in detail above, any quadrangular transmission aperture with dimensions lying between the two stated extreme values can be set up with the new tube. In this embodiment, the height of the side walls and lamellae is 17 cm.

It has already been mentioned that the preliminary diaphragm 18 must be set to the cross-section of the tube. Since the object to be irradiated determines the cross-section of the tube, this tube cross-section is first set up. This setting can be effected manually or by means of servo-motors. Preferably, an adjustable anterior diaphragm is used, and the cross-section of the tube as well as the aperture of the preliminary diaphragm are picked up by actual value indicators, for example potentiometers. The actual values are then compared in comparators and the resulting error signal is used to control the diaphragm servo-motors until the actual values for the diaphragm aperture corresponds to the actual values of the tube cross-section. It will be understood that in this way it is also possible to set up a non-linear relation of tube cross-section to diaphragm aperture.

In a further embodiment of the new tube, an anterior diaphragm 18, forming part of the accelerator, is not required. In this embodiment, the distance between the baseplate and the carrier plates is increased, and diaphragm blocks are mounted on the surfaces, facing the baseplate, of each carrier plate, or the carrier plates are constructed as diaphragm blocks. It will be appreciated that with this embodiment each adjustment of the tube cross-section simultaneously also results in an adjustment of the effective diaphragm aperture.

Finally, it is also possible to adjust the tube cross-section and the diaphragm aperture by means of remote control from an operating panel or from a data store. Appropriate circuits are known to all those skilled in the art and will therefore not be described in detail.

Though the new tube has been described in relation to an illustrated embodiment which possesses four displaceable baseplates and defines a quadrangular transmission aperture, it will be obvious to all those skilled in the art that it is also possible to construct a corresponding tube with three or five or more baseplates which are displaceable symmetrically to one another.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A tube for irradiation equipment for limiting an emergent beam comprising:
   a baseplate having a central aperture and adapted to be attached to the irradiation equipment;
   four carrier plates located parallel to the baseplate, each carrier plate having a beam limiting edge and a sliding edge located at right angles thereto, the limiting edge of each carrier plate resting against the sliding edge of the adjacent carrier plate and means for displacing each of the two mutually opposite pairs of carrier plates parallel to the direction of its sliding edges and symmetrically to the center of a transmission aperture defined by the limiting edges, so as to continuously vary the transmission aperture and so that during which displacement each of the displaced carrier plates carries with it the carrier plate resting against the limiting edge of the displaced carrier plate parallel to the direction of the limiting edge of the resting carrier plate;
   a side wall and at least one equally high lamella provided on each carrier plate, each side wall projecting at the side of the limiting edge abutting the sliding edge at right angles from the respective carrier plate, each lamella being pivotably fastened in the region of the limiting edge and capable of being laid down on the respective carrier plate or of being erected as an extension of the side wall in order to form a side wall of a tube of variable cross-section, each of the carrier plates, side walls, and lamella being opaque to said radiation.

2. The tube recited in claim 1, wherein each lamella includes:
   a steel strip;
   a lamella base fixed to one end of the steel strip and having a bore for pushing the lamella onto a shaft; and
   a plurality of absorption pieces for secondary X-rays and stray electrons fixed in the region of the other end of the steel strip.

3. The tube recited in claim 1 including:
   a plurality of magnets fixed to each carrier plate for holding the lamellae laid down on the carrier plate; and
   a spring engaging at each lamella base to bring the lamellae when released by the holding magnets into a vertical position.

4. The tube recited in claim 1 including:
   a tongue fixed to each carrier plate in the extension of the limiting edge and carrying a stop on an end thereof projecting onto the adjacent carrier plate, one side face of the stop resting against the adjacent erect lamella to prevent the erect lamella from being laid down unintentionally, the other side face of the stop having a wedge-shaped chamfer and being pushed under the next lamella so that when the carrier plate is displaced in order to enlarge the transmission aperture, the wedge serves to lift the next lamella off the holding magnet.

5. The tube recited in claim 1 including:
   an electromagnetic switch device located on each side wall and having a lever for laying down the lamella present on an adjacent carrier plate and adjacent to the side wall onto a carrier plate after a displacement of the carrier plate in order to reduce the transmission aperture.

6. The tube recited in claim 1 including:
   an insulated electrode for a capacitive proximity switch fixed to the free end of each side wall and forming with the side wall a capacitor; and
   means for connecting the capacitor to an HF measuring bridge.

7. The tube recited in claim 1, including:
   means for fixing the entire tube in an insulated manner to the housing of the irradiation equipment to form a capacitive proximity switch; and
   means for connecting the tube to an HF measuring bridge.

8. The tube recited in claim 1 including:
   a plate-shaped tube insert attachable to the casing to form a contact switch;
   at least three stud bolts projecting from the insert, the baseplate including bores for the stud bolts to pass through;
   a plurality of contacts fixed by insulating discs to the baseplate in the region of the bores;
   a plurality of contacts fixed by insulating discs to the free ends of the stud bolts and cooperating with the contacts fixed to the baseplate; and
   a plurality of springs located between the tube insert and the baseplate for pressing the baseplate away from the tube insert and, in order to close the contact switch, for pressing the contacts fixed to the baseplate onto the contacts fixed to the stud bolts.

* * * * *